(12) United States Patent
Seo

(10) Patent No.: US 11,830,591 B2
(45) Date of Patent: Nov. 28, 2023

(54) CHILD CARE INFORMATION PLATFORM SERVER FOR RECOMMENDING INFORMATION REGARDING CHILD CARE BASED ON USER INFORMATION AND THE OPERATING METHOD THEREOF

(71) Applicant: WellnessIntelligence Inc., Seoul (KR)

(72) Inventor: Dong Phil Seo, Yongin-si (KR)

(73) Assignee: WellnessIntelligence Inc., Seoul (KR)

( * ) Notice: Subject to any disclaimer, the term of this patent is extended or adjusted under 35 U.S.C. 154(b) by 598 days.

(21) Appl. No.: 17/105,502

(22) Filed: Nov. 26, 2020

(65) Prior Publication Data
US 2021/0183483 A1    Jun. 17, 2021

(30) Foreign Application Priority Data

Dec. 12, 2019    (KR) ......................... 10-2019-0165305

(51) Int. Cl.
| | | |
|---|---|---|
| *G05B 15/02* | (2006.01) | |
| *G16H 10/60* | (2018.01) | |
| *G16H 20/00* | (2018.01) | |
| *G16H 50/30* | (2018.01) | |

(52) U.S. Cl.
CPC ............. *G16H 10/60* (2018.01); *G05B 15/02* (2013.01); *G16H 20/00* (2018.01); *G16H 50/30* (2018.01)

(58) Field of Classification Search
CPC ........ G16H 10/60; G16H 20/00; G16H 20/30; G16H 20/70; G16H 50/20; G16H 50/30; G05B 15/02
See application file for complete search history.

(56) References Cited

FOREIGN PATENT DOCUMENTS

| | | | |
|---|---|---|---|
| JP | 2018-120527 A | | 8/2018 |
| KR | 10-2016-0005187 A | | 1/2016 |
| KR | 20160005187 A | * | 1/2016 |
| KR | 10-1592021 B1 | | 2/2016 |
| KR | 101592021 B1 | * | 2/2016 |
| KR | 10-2017-0124953 A | | 11/2017 |

* cited by examiner

*Primary Examiner* — Yuhui R Pan
(74) *Attorney, Agent, or Firm* — Park, Kim & Suh, LLC

(57) ABSTRACT

Disclosed are a child care information platform server for recommending information regarding child care based on user information and the operating method thereof. A child care information platform server and the operating method thereof according to an embodiment of the present invention is possible to support recommendation of a child care product for each of a plurality of categories by generating a 3 dimensional characteristic vector based on a mother's personal information and health condition, and a child's health condition which are received from a user terminal, calculating the vector similarity between the 3 dimensional characteristic vector and the predetermined standard vectors of each of the plurality of child products, for each of the plurality of categories, and selecting a recommended child care product wherein the vector similarity of the recommended child care product is biggest among the plurality of child care products.

9 Claims, 3 Drawing Sheets

| | | | |
|---|---|---|---|
| 211 — THE FIRST VALUES (PERSONAL INFORMATION OF A MOTHER) | 30 | 10 | 30 |
| 212 — THE SECOND VALUES (HEALTH INFORMATION OF A MOTHER) | 40 | 30 | 20 |
| 213 — THE THIRD VALUES (HEALTH INFORMATION OF A CHILD) | 40 | 40 | 20 |

220

$$\begin{pmatrix} 30 & 10 & 30 \\ 40 & 30 & 20 \\ 40 & 40 & 20 \end{pmatrix}$$

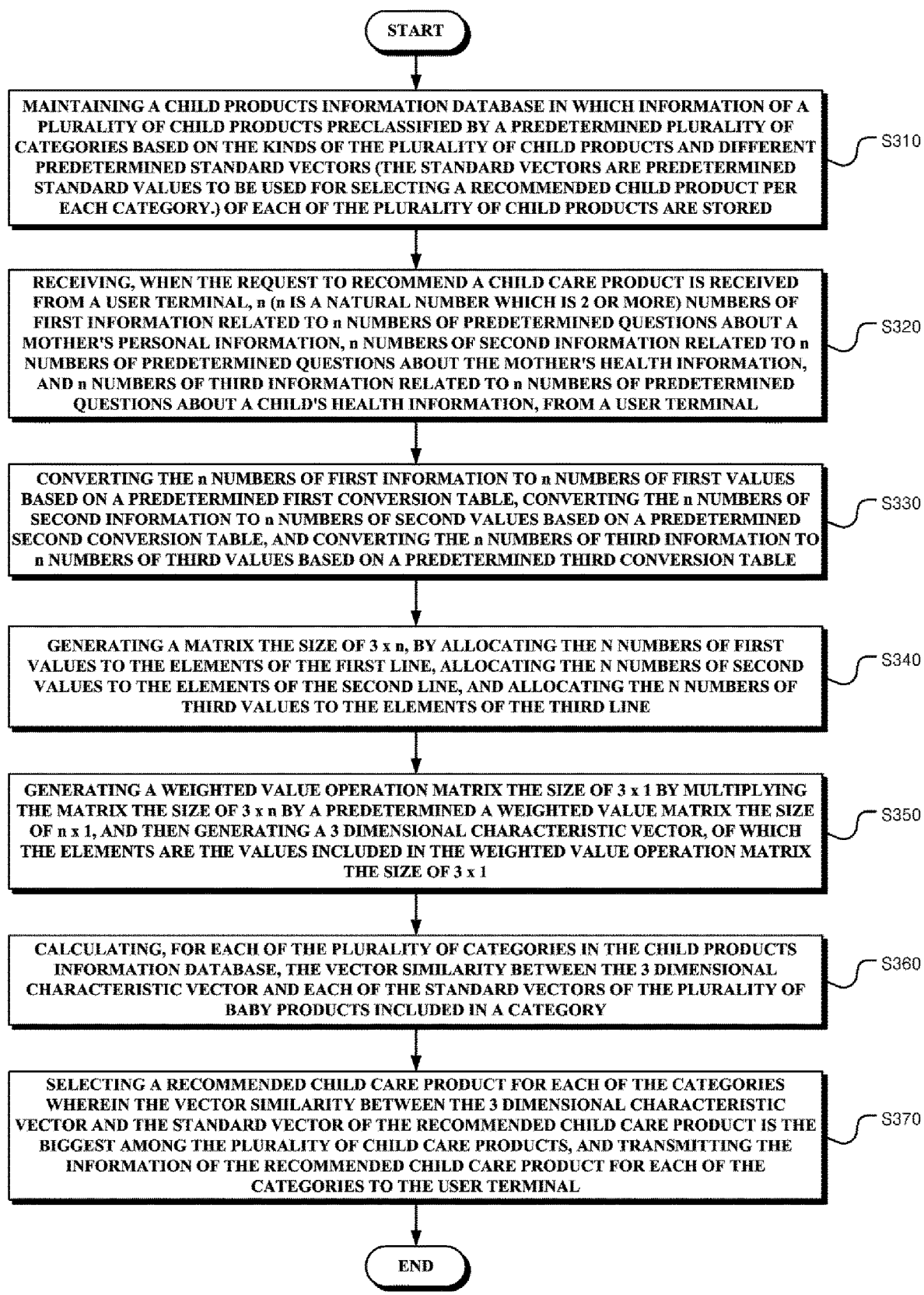

CHILD CARE INFORMATION PLATFORM SERVER FOR RECOMMENDING INFORMATION REGARDING CHILD CARE BASED ON USER INFORMATION AND THE OPERATING METHOD THEREOF

CROSS-REFERENCE TO RELATED APPLICATIONS

This application claims priority to and the benefit of Korean Patent Application No. 10-2019-0165305 filed in the Korean Intellectual Property Office on Dec. 12, 2019, the entire contents of which are incorporated herein by reference.

TECHNICAL FIELD

The present invention relates to a child care information platform server for recommending information regarding child care based on user information and the operating method thereof.

BACKGROUND ART

In recent years, more and more people want to be DINKs which means "Double Income, No Kids". The reason why so many people want to be DINKs differs from each other. Some of them don't try to have a child intentionally because they want to live easygoing and financially free lives. Others want to have a child, but they don't have enough money, time and effort to care a child.

From the aspect of this social trend, it is expected that a lot of pre-parents and parents experience a heavy mental or financial burden to care a child. This social situation may cause the problem of lower childbirth and aging society. Therefore, it is important to find a solution to lessen the burden for pre-parents and parents.

Specifically, providing child care information rapidly may help pre-parents and parents to shorten time for searching for child care information.

Currently, pre-parents and parents mostly communicate with their acquaintances or connect to websites to obtain child care information.

However, pre-parents and parents are able to obtain only limited information from their acquaintances and the information on websites has lower reliability because it may be containing advertisement. Also, there is too much information online, so it is hard for them to extract the information they really need.

In addition, the information from their acquaintances or online should be used only for reference because it is based on other children in the similar situation. Thus, it is almost impossible to find the exact child care information accurately matching to them or their child.

If they can be provided personalized child care information according to a mother's personal information and health condition, and child's health condition, they will be able to obtain child care information much more efficiently. Then, their burden to care a child will be much less than before.

Therefore, there is a need for the research on a technology to recommend child care information based on the mother's personal information and health condition, and the child's health condition.

SUMMARY OF THE INVENTION

A child care information platform server and the operating method thereof according to an embodiment of the present invention is for supporting recommendation of a child care product for each of a plurality of categories by generating a 3 dimensional characteristic vector based on a mother's personal information and health condition, and a child's health condition which are received from a user terminal, calculating the vector similarity between the 3 dimensional characteristic vector and the predetermined standard vectors of each of the plurality of child products, for each of the plurality of categories, and selecting a recommended child care product wherein the vector similarity of the recommended child care product is biggest among the plurality of child care products.

A child care information platform server for recommending information regarding child care based on user information according to an embodiment of the present invention includes: a child products information database in which information of a plurality of child products pre-classified by a predetermined plurality of categories based on the kinds of the plurality of child products and different predetermined standard vectors (the standard vectors are predetermined standard values to be used for selecting a recommended child product per each category.) of each of the plurality of child products are stored; an information receiving unit receiving, when the request to recommend a child care product is received from a user terminal, n (n is a natural number which is 2 or more) numbers of first information related to n numbers of predetermined questions about a mother's personal information, n numbers of second information related to n numbers of predetermined questions about the mother's health information, and n numbers of third information related to n numbers of predetermined questions about a child's health information of, from a user terminal; an information converting unit converting the n numbers of first information to n numbers of first values based on a predetermined first conversion table, converting the n numbers of second information to n numbers of second values based on a predetermined second conversion table, and converting the n numbers of third information to n numbers of third values based on a predetermined third conversion table; a matrix generating unit generating a matrix the size of 3×n, by allocating the n numbers of first values to the elements of the first line, allocating the n numbers of second values to the elements of the second line, and allocating the n numbers of third values to the elements of the third line; a characteristic vector generating unit generating a weighted value operation matrix the size of 3×1 by multiplying the matrix the size of 3×n by a predetermined a weighted value matrix the size of n×1, and then generating a 3 dimensional characteristic vector, of which the elements are the values included in the weighted value operation matrix the size of 3×1; a vector similarity calculating unit calculating, for each of the plurality of categories in the child products information database, the vector similarity between the 3 dimensional characteristic vector and each of the standard vectors of the plurality of baby products included in a category; and a child care product recommending unit selecting the recommended child care product for each of the categories wherein the vector similarity between the 3 dimensional characteristic vector and the standard vector of the recommended child care product is the biggest among the plurality of child care products, and transmitting the information of the recommended child care product for each of the categories to the user terminal.

An operating method of a child care information platform server for recommending information regarding child care based on user information according to an embodiment of the present invention includes: maintaining a child products information database in which information of a plurality of child products pre-classified by a predetermined plurality of categories based on the kinds of the plurality of child products and different predetermined standard vectors (the standard vectors are predetermined standard values to be used for selecting a recommended child product per each category.) of each of the plurality of child products are stored; receiving, when the request to recommend a child care product is received from a user terminal, n (n is a natural number which is 2 or more) numbers of first information related to n numbers of predetermined questions about a mother's personal information, n numbers of second information related to n numbers of predetermined questions about the mother's health information, and n numbers of third information related to n numbers of predetermined questions about a child's health information of, from a user terminal; converting the n numbers of first information to n numbers of first values based on a predetermined first conversion table, converting the n numbers of second information to n numbers of second values based on a predetermined second conversion table, and converting the n numbers of third information to n numbers of third values based on a predetermined third conversion table; generating a matrix the size of 3×n, by allocating the n numbers of first values to the elements of the first line, allocating the n numbers of second values to the elements of the second line, and allocating the n numbers of third values to the elements of the third line; generating a weighted value operation matrix the size of 3×1 by multiplying the matrix the size of 3×n by a predetermined a weighted value matrix the size of n×1, and then generating a 3 dimensional characteristic vector, of which the elements are the values included in the weighted value operation matrix the size of 3×1; calculating, for each of the plurality of categories in the child products information database, the vector similarity between the 3 dimensional characteristic vector and each of the standard vectors of the plurality of baby products included in a category; and selecting the recommended child care product for each of the categories wherein the vector similarity between the 3 dimensional characteristic vector and the standard vector of the recommended child care product is the biggest among the plurality of child care products, and transmitting the information of the recommended child care product for each of the categories to the user terminal.

A child care information platform server and the operating method thereof according to an embodiment of the present invention is possible to support recommendation of a child care product for each of a plurality of categories by generating a 3 dimensional characteristic vector based on a mother's personal information and health condition, and a child's health condition which are received from a user terminal, calculating the vector similarity between the 3 dimensional characteristic vector and the predetermined standard vectors of each of the plurality of child products, for each of the plurality of categories, and selecting a recommended child care product wherein the vector similarity of the recommended child care product is biggest among the plurality of child care products.

BRIEF DESCRIPTION OF THE DRAWINGS

FIG. 2 is a diagram illustrating a child care information platform server for recommending information regarding child care based on user information according to an embodiment of the present invention.

FIG. 3 is a flowchart showing an operating method of a child care information platform server for recommending information regarding child care based on user information according to an embodiment of the present invention.

DETAILED DESCRIPTION

Figure 1:
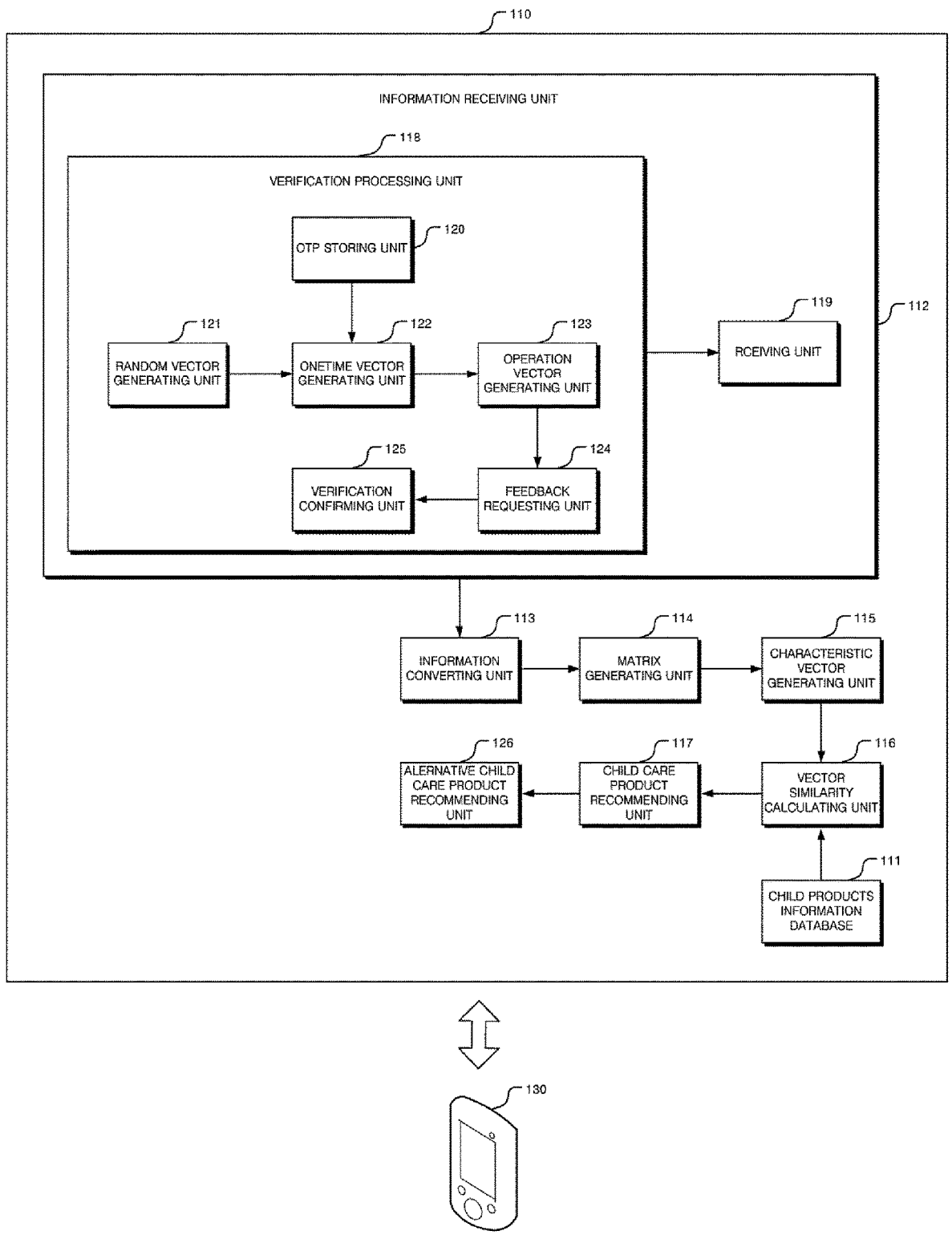
FIG. 1 is a diagram illustrating a structure of a child care information platform server for recommending information regarding child care based on user information according to an embodiment of the present invention.

Hereinafter, embodiments of the present invention will be described in detail with reference to the accompanying drawings. The description does not limit the present invention to specific embodiments, and it should be understood that the present invention covers all the modifications, equivalents and replacements included within the idea and technical scope of the present invention. In describing each drawing, like reference numerals refer to like elements and if it is not contrarily defined, all terms used herein including technological or scientific terms have the same meanings as those generally understood by a person with ordinary skill in the art.

In this document, unless explicitly described to the contrary, the word "comprise" and variations such as "comprises" or "comprising", will be understood to imply the inclusion of stated elements but not the exclusion of any other elements. Further, in various embodiments of the present invention, each of components, functional blocks or means may be constituted by one or more lower components and electrical, electronic, and mechanical functions performed by respective components may be implemented as various known devices or mechanical elements including an electronic circuit, an integrated circuit, an Application Specific Integrated Circuit (ASIC), etc., and the respective components may be separately implemented or two or more components may be integrated into one and implemented.

Meanwhile, blocks of the accompanying block diagram or steps of a flowchart may be appreciated as meaning computer program instructions mounted on a processor or a memory of data processible equipment such as a universal computer, a special computer, a portable notebook computer, a network computer, etc., and performing designated functions. Since the computer program instructions may be stored in a memory provided in a computer device or a computer readable memory, functions described in blocks of a block diagram or steps of a flowchart may be produced as a manufactured object including an instruction mean performing the functions. Moreover, each block or each step may represent a part of a module, a segment, or a code that includes one or more executable instructions for executing a specified logical function(s). It should also be noted that in some replaceable embodiments, the functions mentioned in the blocks or steps may also be executed differently from a predetermined order. For example, two blocks or steps that are sequentially illustrated are substantially simultaneously carried out, or may be performed in a reverse order, and in some cases, the blocks or steps may be performed while some blocks or steps are omitted.

FIG. 1 is a diagram illustrating a structure of a child care information platform server for recommending information regarding child care based on user information according to an embodiment of the present invention.

Referring to FIG. 1, a child care information platform server 110 for recommending information regarding child care based on user information according to an embodiment of the present invention includes a child products information database 111, an information receiving unit 112, an information converting unit 113, a matrix generating unit 114, a characteristic vector generating unit 115, a vector similarity calculating unit 116, and a child care product recommending unit 117.

Information of a plurality of child products pre-classified by a predetermined plurality of categories based on the kinds of the plurality of child products and different predetermined standard vectors are stored in the child products information database 111.

Here, the standard vectors are predetermined standard values to be used for selecting a recommended child product per each category.

For example, information as shown in Table 1 below may be stored in the child products information database 111.

TABLE 11

| Category | Child Care Product | Standard Vector |
|---|---|---|
| Toys | Blocks | [a1 a2 a3] |
| | Xylophones | [a4 a5 a6] |
| | Robots | [a7 a8 a9] |
| | Dolls | [a10 a11 a12] |
| | Sound-books | [a13 a14 a15] |
| Products for Sleep | Vests | [b1 b2 b3] |
| | Pajamas | [b4 b5 b6] |
| | Socks | [b7 b8 b9] |
| | Humidifiers | [b10 b11 b12] |
| | White Noise | [b13 b14 b15] |
| ... | ... | ... |

When the request to recommend a child care product is received from a user terminal 130, the information receiving unit 112 receives n (n is a natural number which is 2 or more) numbers of first information related to n numbers of predetermined questions about a mother's personal information, n numbers of second information related to n numbers of predetermined questions about the mother's health information, and n numbers of third information related to n numbers of predetermined questions about a child's health information of, from the user terminal 130.

For example, let's suppose that n is '3', '3' numbers of questions about a mother's personal information are 'the mother's age, the mother's residence, the mother's weight', '3' numbers of questions about the mother's health condition are 'the mother's temperature, the mother's systolic pressure, the mother's pulse rate', and '3' numbers of questions about a child's health condition are 'the child's temperature, the child's weight, the child's number of times having faeces'.

Then, when the request to recommend a child care product is received from the user terminal 130, the information receiving unit 112 may receive '3' numbers of first information about 'the mother's age, the mother's residence, the mother's weight', receive '3' numbers of second information about 'the mother's temperature, the mother's systolic pressure, the mother's pulse', and '3' numbers of third information about 'the child's temperature, the child's weight, the child's number of times having faeces, from the user terminal 130.

In this case, according to an embodiment of the present invention, the information receiving unit may include a verification processing unit 118 and a receiving unit 119.

When the request to recommend a child care product is received from the user terminal 130, the verification processing unit 118 processes verification for the user terminal 130.

In this case, according to an embodiment of the present invention, the verification processing unit 118 may include an OTP storing unit 120, a random vector generating unit 121, a onetime vector generating unit 122, an operation vector generating unit 123, a feedback requesting unit 124, and a verification confirming unit 125 to verify the user terminal 130 when the request to recommend a child care product is received from the user terminal 130.

A predetermined OTP (One Time Password) generating function for generating k (k is a natural number which is 2 or more) numbers of onetime passwords according to the time value of the present is stored in the OTP storing unit 120.

Here, OTP means a onetime certification code which is randomly generated instead of fixed password, and the OTP generating function may be predetermined by a developer to generate a onetime certification code according to the time value of the present.

When the request to recommend a child care product is received from the user terminal 130, the random vector generating unit 121 randomly generates a k dimensional random vector to be used for verifying the user.

The onetime vector generating unit 122 generates k numbers of first onetime certification codes according to the time value of the present, based on the OTP generating function and generates a k dimensional onetime vector of which the elements are the k numbers of first onetime certification codes.

The operation vector generating unit 123 generates a k dimensional operation vector by calculating Hadamard product between the k dimensional random vector and the k dimensional onetime vector.

Here, Hadamard product means an operation to multiply each of the elements of two matrixes or vectors which have the same size. When there are vectors of '[a b c]' and '[x y z]', Hadamard product between the two vectors may be shown as '[ax by cz]'.

For example, let's suppose k is '5', a '5' dimensional random vector randomly generated by the random vector generating unit 121 is '[0 1 2 3 4]', and '5' numbers of first onetime certification codes generated by the onetime vector generating unit 122 as based on the OTP generating function are '1', '2', '3', '4', '5'. Then, the onetime vector generating unit 122 may generate '[1 2 3 4 5]' as a '5' dimensional onetime vector of which the elements are '1', '2', '3', '4', '5', the '5' numbers of first onetime certification codes.

The operation vector generating unit 123 may generate '[0 2 6 12 20]' as a '5' dimensional operation vector by calculating Hadamard product between '[0 1 2 3 4]' which is the '5' dimensional random vector and '[1 2 3 4 5]' which is the '5' dimensional onetime vector.

The feedback requesting unit 124 transmits the k dimensional operation vector to the user terminal 130, and requests the user terminal 130 to transmit a feedback vector corresponded to the k dimensional operation vector.

In this case, according to the embodiment of the present invention, an OTP generating function for verifying which is the same as the OTP generating function may be stored in the memory of the user terminal 130.

Also, when the k dimensional operation vector is received from the child care information platform server 110, the user terminal 130 may generate the k numbers of certification codes for verifying based on the OTP generating function for verifying which is stored in the memory of the user terminal 130, generate the k dimensional vector for verifying of which elements are the inverse numbers of k numbers of certification codes for verifying, and generate the k dimensional feedback vector by calculating Hadamard product between the k dimensional operation vector and the k dimensional vector for verifying. Then, the user terminal 130 may transmit the k dimensional first feedback vector to the child care information platform server 110.

In this regard, as the example explained above, when the '5' dimensional operation vector is '[0 2 6 12 20]', the user terminal 130 may generate '1', '2', '3', '4', '5' which are certification codes for verifying according to the time value of the present, based on the OTP generating function for verifying which is stored in the memory of the user terminal 130. Then, the user terminal 130 may generate '[1 ½ 1/3 ¼ ⅕]' as a '5' dimensional vector for verifying of which the elements are the inverse numbers of the certification codes for verifying.

Also, the user terminal 130 may generate '[0 1 2 3 4]' as a '5' dimensional first feedback vector by calculating '[0 2 6 12 20]' which is the '5' dimensional operation vector and '[1 ½ 1/3 ¼ ⅕]' which is the '5' dimensional vector for verifying. Then, the user terminal 130 may transmit '[0 1 2 3 4]' which is the first feedback vector to the child care information platform server 110.

When the k dimensional first feedback vector, as a feedback vector corresponded to the k dimensional operation vector, is received from the user terminal 130, the verification confirming unit 125 completes the verification for the user terminal 130 by confirming if the k dimensional first vector is the same as the k dimensional random vector.

For example, as the example explained above, when the '5' dimensional random vector is '[0 1 2 3 4]' and the '5' dimensional first feedback vector, received from the user terminal 130, is '[0 1 2 3 4]', the verification confirming unit 125 may complete the verification for the user terminal 130 by confirming if '[0 1 2 3 4]' which is the '5' dimensional first vector is the same as '[0 1 2 3 4]' which is the '5' dimensional random vector.

As such, when the verification for the user terminal 130 is completed, the receiving unit 119 receives the n numbers of first information, the n numbers of second information, and then numbers of third information, from the user terminal 130.

The information converting unit 113 converts the n numbers of first information to n numbers of first values based on a predetermined first conversion table, coverts the n numbers of second information to n numbers of second values based on a predetermined second conversion table, and converts the n numbers of third information to the n numbers of third values based on a predetermined third conversion table.

In this regard, information as shown in Table 2 below may be recorded in the first conversion table, information as shown in Table 3 below may be recorded in the second conversion table, and information as shown in Table 4 below may be recorded in the third conversion table.

TABLE 2

| the Mother's Age (years) | | the Mother's Residence | | the Mother's Weight (kg) | |
|---|---|---|---|---|---|
| ~20 | 10 | Seoul/Gyeonggi | 10 | ~40 | 10 |
| 21~30 | 20 | Gangwon | 20 | 40~50 | 20 |
| 31~40 | 30 | Chungcheong | 30 | 50~60 | 30 |
| 41~50 | 40 | Jeonla | 40 | 60~70 | 40 |
| 51~60 | 50 | Gyeongsang | 50 | 70~80 | 50 |
| 61~ | 60 | Jeju | 60 | 80~ | 60 |

TABLE 3

| the Mother's Temperature (° C.) | | the Mother's Systolic Pressure (mmHg) | | the Mother's Pulse Rate (times/min) | |
|---|---|---|---|---|---|
| ~35 | 10 | ~90 | 10 | ~40 | 10 |
| 35~36 | 20 | 90~110 | 20 | 40~60 | 20 |
| 36~37 | 30 | 110~130 | 30 | 60~80 | 30 |
| 37~38 | 40 | 130~150 | 40 | 80~100 | 40 |
| 38~39 | 50 | 150~170 | 50 | 100~120 | 50 |
| 39~ | 60 | 170~ | 60 | 120~ | 60 |

TABLE 4

| the Child's Temperature (° C.) | | the Child's Weight (kg) | | the Child's Number of Times Having Faeces | |
|---|---|---|---|---|---|
| ~35 | 10 | ~3 | 10 | ~1 | 10 |
| 35~36 | 20 | 3~4 | 20 | 2 | 20 |
| 36~37 | 30 | 4~5 | 30 | 3 | 30 |
| 37~38 | 40 | 5~6 | 40 | 4 | 40 |
| 38~39 | 50 | 6~7 | 50 | 5 | 50 |
| 39~ | 60 | 7~ | 60 | 6~ | 60 |

In this case, the information converting unit 113 may convert the '3' numbers of first information to '3' numbers of first values based on the first conversion table as shown in Table 2 above, convert the '3' numbers of second information to '3' numbers of second values based on the second conversion table as shown in Table 3 above, and convert the '3' numbers of third information to '3' numbers of third values based on the predetermined third conversion table as shown in Table 4 above.

The matrix generating unit 114 generates a matrix the size of 3×n, by allocating the n numbers of first values to the elements of the first line, allocating the n numbers of second values to the elements of the second line, and allocating the n numbers of third values to the elements of the third line.

The characteristic vector generating unit 115 generates a weighted value operation matrix the size of 3×1 by multiplying the matrix the size of 3×n by a predetermined a weighted value matrix the size of n×1, and then generates a 3 dimensional characteristic vector, of which the elements are the values included in the weighted value operation matrix the size of 3×1.

In this case, according to an embodiment of the present invention, each of n numbers of weighted value elements of the weighted value matrix the size of n×1 may be a value which is more than 0 and less than 1, and the sum of the n numbers of weighted value elements may be 1.

Here, the weighted value matrix may be predetermined by the developer, and may be used to calculate a weighted average of values about the mother's personal information and health condition, and the child's health condition.

The vector similarity calculating unit 116 calculates the vector similarity between the 3 dimensional characteristic vector and each of the standard vectors of the plurality of baby products included in a category, for each of the plurality of categories in the child products information database.

In this case, according to an embodiment of the present invention, the vector similarity may be calculated according to the Equation 1 below.

$$M = C + \frac{1}{D+1}$$ [Equation 1]

Here, M means the vector similarity between two vectors, C means cosine similarity between the two vectors, and D means Euclidean distance between the two vectors. C may be calculated according to the Equation 2 below, and D may be calculated according to the Equation 3 below.

$$C = \frac{\sum_{i=1}^{n} A_i \times B_i}{\sqrt{\sum_{i=1}^{n}(A_i)^2} \times \sqrt{\sum_{i=1}^{n}(B_i)^2}}$$ [Equation 2]

Here, C means the cosine similarity between vector A and vector B, and C is the value between −1 and 1. The bigger C means that vector A is more similar to vector B. Also, $A_i$ means i-th element of the vector A and $B_i$ means i-th element of the vector B.

$$D = \sqrt{\sum_{i=1}^{n}(p_i - q_i)^2}$$ [Equation 3]

Here, D means Euclidean distance, $p_i$ is the i-th element of vector A, and $q_i$ means i-th element of vector B. The shorter Euclidean distance between vector A and vector B means that vector A is more similar to vector B.

The child care product recommending unit 117 selects a recommended child care product for each of the categories, wherein the vector similarity between the 3 dimensional characteristic vector and the standard vector of the recommended child care product is the biggest among the plurality of child care products. Then, the child care product recommending unit 117 transmits the information of the recommended child care product for each of the categories to the user terminal 130.

Below is the explanation of the child care information platform server 110, referring to FIG. 2.

First, following the example explained above, let's suppose that the information converting unit 113 converted the '3' numbers of first information to '3' numbers of first values 211, the '3' numbers of second information to '3' numbers of second values 212, and the '3' numbers of third information to '3' numbers of third values 213, as shown in 210 of FIG. 2.

In this case, the matrix generating unit 114 may generate a matrix the size of 3×'3', by allocating the '3' numbers of first values 211 to the elements of the first line, allocating the '3' numbers of second values 212 to the elements of the second line, and allocating the '3' numbers of third values 213 to the elements of the third line.

Then, the characteristic vector generating unit 115 may generate a weighted value operation matrix the size of '3'×1 by multiplying the matrix the size of 3×'3' by a predetermined a weighted value matrix the size of '3'×1. After that, the characteristic vector generating unit 115 may generate a 3 dimensional characteristic vector, of which the elements are the values included in the weighted value operation matrix the size of 3×1.

For example, when the weighted value matrix the size of '3'×1 is $$\begin{pmatrix} 0.3 \\ 0.4 \\ 0.3 \end{pmatrix},$$

the characteristic vector generating unit 115 may generate a weighted value operation matrix the size of '3'×1 by operating according to Equation 4 below.

$$\begin{pmatrix} 30 & 10 & 30 \\ 40 & 30 & 20 \\ 40 & 40 & 20 \end{pmatrix} \times \begin{pmatrix} 0.3 \\ 0.4 \\ 0.3 \end{pmatrix} = \begin{pmatrix} 22 \\ 30 \\ 34 \end{pmatrix}$$ [Equation 4]

As such, when the weighted value operation matrix the size of '3'×1 is generated, the characteristic vector generating unit 115 may generate a '3' dimensional characteristic vector '[22 30 34]', of which the elements are '22', '30', '34', the values included in the weighted value operation matrix the size of '3'×1.

After that, the vector similarity calculating unit 116 may calculate the vector similarity between '[22 30 34]' which is the 3 dimensional characteristic vector and each of the standard vectors of the plurality of baby products included in a category, for each of the plurality of categories in the child products information database.

Specifically, for the 'toys' category, the vector similarity calculating unit 116 may calculate the vector similarity between '[22 30 34]' which is the 3 dimensional characteristic vector and '[a1 a2 a3]' which is the standard vector corresponded to 'blocks' included in the 'toys' category, the vector similarity between '[22 30 34]' and '[a4 a5 a6]' which is the standard vector corresponded to 'xylophones' included in the 'toys' category, and the vector similarity between '[22 30 34]' and '[a7 a8 a9]' which is the standard vector corresponded to 'robots' included in the 'toys' category. Also, the vector similarity calculating unit 116 may calculate the vector similarity between '[22 30 34]' and '[a10 a11 a12]' which is the standard vector corresponded to 'dolls' included in the 'toys' category, and the vector similarity between '[22 30 34]' and '[a13 a14 a15]' which is the standard vector corresponded to 'sound-books' included in the 'toys' category.

Then, the child care product recommending unit 117 may select a recommended child care product for each of the categories wherein the vector similarity between '[22 30 34]' and the standard vector of the recommended child care product is the biggest among the plurality of child care products. Then, the child care product recommending unit 117 may transmit the information of the recommended child care product for each of the categories to the user terminal 130.

Specifically, for the 'toys' category, when the vector similarity between '[22 30 34]' and the standard vector corresponded to 'sound-books' is the biggest among 'blocks, xylophones, robots, dolls, sound-books' which are included in the 'toys' category, the child care product recommending unit 117 may select 'sound-books' as the recommended child care product for the 'toys' category. Then, the child care product recommending unit 117 may transmit the information of 'sound-books' to the user terminal 130.

In the same way, for the other categories, the child care product recommending unit 117 may select a recommended child care product and transmit the information of the selected recommended child care product to the user terminal 130.

Also, according to an embodiment of the present invention, the child care information platform server 110 may further include an alternative child care product recommending unit 126.

When the request to recommend an alternative child care product for a first category among the plurality of categories is received from the user terminal 130 after the information of the recommended child care product for each of the categories is sent to the user terminal 130, the alternative child care product recommending unit 126 selects an alternative child care product for the first category wherein the vector similarity between the 3 dimensional characteristic vector and the standard vector corresponded to the alternative child care product is the second biggest among the plurality of child care products included in the first category. Then, the alternative child care product recommending unit 126 transmits the information of the alternative child care product for the first category to the user terminal 130.

For example, following the example explained above, when the request to recommend an alternative child care product for the 'toys' category instead of 'sound-books' is received from the user terminal 130 after the information of the recommended child care product for each of the categories is sent to the user terminal 130, the alternative child care product recommending unit 126 may select an alternative child care product for the 'toys' category wherein the vector similarity between '[22 30 34]' which is the 3 dimensional characteristic vector and the standard vector corresponded to the alternative child care product is the second biggest 'blocks, xylophones, robots, dolls, sound-books' included in the 'toys' category. Then, the alternative child care product recommending unit 126 may transmit the information of the alternative child care product for the first category to the user terminal 130.

That is, if the user wants to receive the information of other child care product for the first category after the user received the information of the recommended child care product for each of the categories through the user terminal 130, the alternative child care product recommending unit 126 may support the user to receive diverse information through the user terminal 130, by transmitting the information of the alternative child care product for the first category.

Also, according to an embodiment of the present invention, the child care information platform server 110 may support recommendation of the exercise treatment for the mother based on the mother's personal information and health condition, the vaccination schedule for child and the community hospital based on the child's health condition.

FIG. 3 is a flowchart showing an operating method of a child care information platform server for recommending information regarding child care based on user information according to an embodiment of the present invention.

In step S310, a child products information database is maintained, in which information of a plurality of child products pre-classified by a predetermined plurality of categories based on the kinds of the plurality of child products and different predetermined standard vectors (the standard vectors are predetermined standard values to be used for selecting a recommended child product per each category.) of each of the plurality of child products are stored.

In step S320, when the request to recommend a child care product is received from a user terminal, n (n is a natural number which is 2 or more) numbers of first information related to n numbers of predetermined questions about a mother's personal information, n numbers of second information related to n numbers of predetermined questions about the mother's health information, and n numbers of third information related to n numbers of predetermined questions about a child's health information are received from a user terminal.

In step S330, the n numbers of first information are converted to n numbers of first values based on a predetermined first conversion table, the n numbers of second information are converted to n numbers of second values based on a predetermined second conversion table, and the n numbers of third information are converted to n numbers of third values based on a predetermined third conversion table.

In step S340, a matrix the size of 3×n is generated by allocating the n numbers of first values to the elements of the first line, allocating the n numbers of second values to the elements of the second line, and allocating the n numbers of third values to the elements of the third line.

In step S350, a weighted value operation matrix the size of 3×1 is generated by multiplying the matrix the size of 3×n by a predetermined a weighted value matrix the size of n×1, and then a 3 dimensional characteristic vector is generated, of which the elements are the values included in the weighted value operation matrix the size of 3×1.

In step S360, the vector similarity between the 3 dimensional characteristic vector and each of the standard vectors of the plurality of baby products included in a category is calculated for each of the plurality of categories in the child products information database.

In step S370, a recommended child care product for each of the categories is selected, wherein the vector similarity between the 3 dimensional characteristic vector and the standard vector of the recommended child care product is the biggest among the plurality of child care products, and the information of the recommended child care product for each of the categories is transmitted to the user terminal.

In this case, according to an embodiment of the present invention, each of n numbers of weighted value elements of the weighted value matrix the size of n×1 may be a value which is more than 0 and less than 1, and the sum of the n numbers of weighted value elements may be 1.

Also, according to an embodiment of the present invention, the vector similarity may be calculated based on the Equation 1 above.

Also, according to an embodiment of the present invention, step S320 may include processing, when the request to recommend a child care product is received from the user terminal, verification for the user terminal, and receiving, when the verification for the user terminal is completed, the n numbers of first information, the n numbers of second information, and the n numbers of third information, from the user terminal.

In this case, according to an embodiment of the present invention, processing verification for the user terminal may include maintaining an OTP (One Time Password) storing unit storing a predetermined OTP generating function for generating k (k is a natural number which is 2 or more) numbers of onetime passwords according to the time value of the present, randomly generating, when the request to recommend a child care product is received from the user terminal, a k dimensional random vector to be used for verifying the user, generating k numbers of first onetime certification codes according to the time value of the present, based on the OTP generating function, and generating a k dimensional onetime vector of which the elements are the k numbers of first onetime certification codes, generating a k dimensional operation vector by calculating Hadamard product between the k dimensional random vector and the k dimensional onetime vector, transmitting the k dimensional operation vector to the user terminal and requesting the user terminal to transmit a feedback vector corresponded to the k dimensional operation vector, and completing, when the k dimensional first feedback vector (the k dimensional first feedback vector is a vector generated by generating k numbers of certification codes for verifying based on a OTP generating function for verifying, which is the same as the OTP generating function and pre-stored in the memory of the user terminal, generating a k dimensional vector for verifying of which the elements are the inverse numbers of the k numbers of certification codes for verifying, and calculating Hadamard product between the k dimensional operation vector and the k dimensional vector for verifying) is received from the user terminal, the verification for the user terminal by confirming if a k dimensional first vector is the same as the k dimensional random vector.

Also, according to an embodiment of the present invention, the user terminal may store a OTP generating function for verifying which is the same as the OTP generating function in the memory, and when the k dimensional operation vector is received from the child care information platform server, may generate and generates the k numbers of certification codes for verifying based on the OTP generating function for verifying which is stored in the memory of the user terminal, generates the k dimensional vector for verifying of which elements are the inverse numbers of the k numbers of certification codes for verifying, generates the k dimensional feedback vector by calculating Hadamard product between the k dimensional operation vector and the k dimensional vector for verifying, and then transmitting the k dimensional first feedback vector to the child care information platform server.

Also, according to an embodiment of the present invention, the operating method of a child care information platform server may further include selecting, when the request to recommend an alternative child care product for a first category among the plurality of categories is received from the user terminal after the information of the recommended child care product for each of the categories is sent to the user terminal, an alternative child care product for the first category wherein the vector similarity between the 3 dimensional characteristic vector and the standard vector corresponded to the alternative child care product is the second biggest among the plurality of child care products included in the first category, and transmitting the information of the alternative child care product for the first category to the user terminal.

Hereinabove, referring to FIG. 3, the operating method of the child care information platform server for recommending information regarding child care based on user information according to an embodiment of the present invention is described. Here, since the operating method of the child care information platform server according to an embodiment of the present invention may correspond to a configuration for an operation of the child care information platform server 110 for recommending information regarding child care based on user information described by using FIG. 1, a more detailed description thereof will be omitted.

The operating method of the child care information platform according to an embodiment of the present invention may be implemented by a computer program stored in a storage medium, which is used to execute the operating method through a combination with a computer.

Further, the operating method of the child care information platform server according to an embodiment of the present invention may be implemented in a program command type which may be performed through various computer means and recorded in a computer readable medium. The computer readable medium may singly or combinationally include a program command, a data file, or a data structure or a combination thereof. The program command recorded in the medium may be specially designed and configured for the present invention, or may be publicly known to and used by those skilled in the computer software field. Examples of the computer-readable recording medium include magnetic media such as a hard disk, a floppy disk, and a magnetic tape, optical media such as a CD-ROM and a DVD, magneto-optical media such as a floptical disk, and a hardware device which is specifically configured to store and execute the program command such as a ROM, a RAM, and a flash memory. Examples of the program command include a high-level language code executable by a computer by using an interpreter, and the like, as well as a machine language code created by a compiler.

As described above, the present invention has been described by specified matters such as detailed components, and the like and limited embodiments and drawings, but the description is just provided to assist more overall understanding of the present invention and the present invention is not limited to the embodiment and various modifications and changes can be made by those skilled in the art from such a disclosure.

Accordingly, the spirit of the present invention should not be defined only by the described embodiments, and it should be appreciated that claims to be described below and all things which are equivalent to the claims or equivalently modified to the claims are included in the scope of the spirit of the present invention.

What is claimed is:

1. A child care information platform server for recommending information regarding child care based on user information, the child care information platform server comprising:
  a child products information database in which information of a plurality of child products pre-classified by a predetermined plurality of categories based on the kinds of the plurality of child products and different predetermined standard vectors of each of the plurality of child products are stored, wherein the standard vectors are predetermined standard values to be used for selecting a recommended child product per each category;
  an information receiving unit receiving, when a request to recommend a child care product is received from a user terminal, n numbers of first information related to n numbers of predetermined questions about a mother's personal information, n numbers of second information related to n numbers of predetermined questions about a mother's health information, and n numbers of third information related to n numbers of predetermined questions about a child's health information, from a user terminal, wherein n is a natural number which is 2 or more;
  an information converting unit converting the n numbers of first information to n numbers of first values based on a predetermined first conversion table, converting the n numbers of second information to n numbers of second values based on a predetermined second conversion table, and converting the n numbers of third information to n numbers of third values based on a predetermined third conversion table;
  a matrix generating unit generating a matrix the size of 3×n, by allocating the n numbers of first values to the elements of the first line, allocating the n numbers of second values to the elements of the second line, and allocating the n numbers of third values to the elements of the third line;

a characteristic vector generating unit generating a weighted value operation matrix the size of 3×1 by multiplying the matrix the size of 3×n by a predetermined a weighted value matrix the size of n×1, and then generating a 3 dimensional characteristic vector, of which the elements are the values included in the weighted value operation matrix the size of 3×1;

a vector similarity calculating unit calculating, for each of the plurality of categories in the child products information database, the vector similarity between the 3 dimensional characteristic vector and each of the standard vectors of the plurality of baby products included in a category; and a child care product recommending unit selecting a recommended child care product for each of the categories wherein the vector similarity between the 3 dimensional characteristic vector and the standard vector of the recommended child care product is the biggest among the plurality of child care products, and transmitting the information of the recommended child care product for each of the categories to the user terminal, wherein the vector similarity is calculated based on the Equation 1 below:

$$M = C + \frac{1}{D+1},$$ [Equation 1]

wherein M means the vector similarity between two vectors, C means cosine similarity between the two vectors, and D means Euclidean distance between the two vectors.

2. The child care information platform server of claim 1, wherein each of n numbers of weighted value elements of the weighted value matrix the size of n×1 is a value which is more than 0 and less than 1, and the sum of the n numbers of weighted value elements is 1.

3. The child care information platform server of claim 1, wherein the information receiving unit includes
   a verification processing unit processing, when the request to recommend a child care product is received from the user terminal, verification for the user terminal, and
   a receiving unit receiving, when the verification for the user terminal is completed, the n numbers of first information, the n numbers of second information, and the n numbers of third information, from the user terminal,
   wherein the verification processing unit includes
   an OTP (One Time Password) storing unit storing a predetermined OTP generating function for generating k numbers of onetime passwords according to the time value of the present, wherein k is a natural number which is 2 or more,
   a random vector generating unit randomly generating, when the request to recommend a child care product is received from the user terminal, a k dimensional random vector to be used for verifying the user,
   a onetime vector generating unit generating k numbers of first onetime certification codes according to the time value of the present, based on the OTP generating function, and generating a k dimensional onetime vector of which the elements are the k numbers of first onetime certification codes,
   an operation vector generating unit generating a k dimensional operation vector by calculating Hadamard product between the k dimensional random vector and the k dimensional onetime vector,
   a feedback requesting unit transmitting the k dimensional operation vector to the user terminal and requesting the user terminal to transmit a feedback vector corresponded to the k dimensional operation vector, and
   a verification confirming unit completing, when a k dimensional first feedback vector, which is a vector generated by generating k numbers of certification codes for verifying based on a OTP generating function for verifying, which is the same as the OTP generating function and pre-stored in the memory of the user terminal, generating a k dimensional vector for verifying of which the elements are the inverse numbers of the k numbers of certification codes for verifying, and calculating Hadamard product between the k dimensional operation vector and the k dimensional vector for verifying, is received from the user terminal, the verification for the user terminal by confirming if the k dimensional first vector is the same as the k dimensional random vector, and
   wherein the user terminal stores a OTP generating function for verifying which is the same as the OTP generating function in the memory, and generates, when the k dimensional operation vector is received from the child care information platform server, the k numbers of certification codes for verifying based on the OTP generating function for verifying which is stored in the memory of the user terminal, generates the k dimensional vector for verifying of which elements are the inverse numbers of the k numbers of certification codes for verifying, generates the k dimensional feedback vector by calculating Hadamard product between the k dimensional operation vector and the k dimensional vector for verifying, and then transmitting the k dimensional first feedback vector to the child care information platform server.

4. The child care information platform server of claim 1, further comprising:
   an alternative child care product recommending unit selecting, when the request to recommend an alternative child care product for a first category among the plurality of categories is received from the user terminal after the information of the recommended child care product for each of the categories is sent to the user terminal, an alternative child care product for the first category wherein the vector similarity between the 3 dimensional characteristic vector and the standard vector corresponded to the alternative child care product is the second biggest among the plurality of child care products included in the first category, and transmitting the information of the alternative child care product for the first category to the user terminal.

5. An operating method of a child care information platform server for recommending information regarding child care based on user information, the operating method comprising:
   maintaining a child products information database in which information of a plurality of child products pre-classified by a predetermined plurality of categories based on the kinds of the plurality of child products and different predetermined standard vectors of each of the plurality of child products are stored, wherein the standard vectors are predetermined standard values to be used for selecting a recommended child product per each category;

receiving, when a request to recommend a child care product is received from a user terminal, n numbers of first information related to n numbers of predetermined questions about a mother's personal information, n numbers of second information related to n numbers of predetermined questions about a mother's health information, and n numbers of third information related to n numbers of predetermined questions about a child's health information, from a user terminal, wherein n is a natural number which is 2 or more;

converting the n numbers of first information to n numbers of first values based on a predetermined first conversion table, converting the n numbers of second information to n numbers of second values based on a predetermined second conversion table, and converting the n numbers of third information to n numbers of third values based on a predetermined third conversion table;

generating a matrix the size of 3×n, by allocating the n numbers of first values to the elements of the first line, allocating the n numbers of second values to the elements of the second line, and allocating the n numbers of third values to the elements of the third line;

generating a weighted value operation matrix the size of 3×1 by multiplying the matrix the size of 3×n by a predetermined a weighted value matrix the size of n×1, and then generating a 3 dimensional characteristic vector, of which the elements are the values included in the weighted value operation matrix the size of 3×1;

calculating, for each of the plurality of categories in the child products information database, the vector similarity between the 3 dimensional characteristic vector and each of the standard vectors of the plurality of baby products included in a category; and selecting a recommended child care product for each of the categories wherein the vector similarity between the 3 dimensional characteristic vector and the standard vector of the recommended child care product is the biggest among the plurality of child care products, and transmitting the information of the recommended child care product for each of the categories to the user terminal, wherein the vector similarity is calculated based on the Equation 1 below:

$$M = C + \frac{1}{D+1},$$ [Equation 1]

wherein M means the vector similarity between two vectors, C means cosine similarity between the two vectors, and D means Euclidean distance between the two vectors.

6. The operating method of claim 5, wherein each of n numbers of weighted value elements of the weighted value matrix the size of n×1 is a value which is more than 0 and less than 1, and the sum of the n numbers of weighted value elements is 1.

7. The operating method of claim 5, wherein the receiving the n numbers of first information, the n numbers of second information and the n numbers of third information, from the user terminal includes processing, when the request to recommend a child care product is received from the user terminal, verification for the user terminal, and receiving, when the verification for the user terminal is completed, the n numbers of first information, the n numbers of second information, and the n numbers of third information, from the user terminal, wherein the processing verification for the user terminal includes maintaining an OTP (One Time Password) storing unit storing a predetermined OTP generating function for generating k numbers of onetime passwords according to the time value of the present, wherein k is a natural number which is 2 or more, randomly generating, when the request to recommend a child care product is received from the user terminal, a k dimensional random vector to be used for verifying the user, generating k numbers of first onetime certification codes according to the time value of the present, based on the OTP generating function, and generating a k dimensional onetime vector of which the elements are the k numbers of first onetime certification codes, generating a k dimensional operation vector by calculating Hadamard product between the k dimensional random vector and the k dimensional onetime vector, transmitting the k dimensional operation vector to the user terminal and requesting the user terminal to transmit a feedback vector corresponded to the k dimensional operation vector, and completing, when a k dimensional first feedback vector, which is a vector generated by generating k numbers of certification codes for verifying based on a OTP generating function for verifying, which is the same as the OTP generating function and pre-stored in the memory of the user terminal, generating a k dimensional vector for verifying of which the elements are the inverse numbers of the k numbers of certification codes for verifying, and calculating Hadamard product between the k dimensional operation vector and the k dimensional vector for verifying, is received from the user terminal, the verification for the user terminal by confirming if the k dimensional first vector is the same as the k dimensional random vector, and wherein the user terminal stores a OTP generating function for verifying which is the same as the OTP generating function in the memory, and generates, when the k dimensional operation vector is received from the child care information platform server, the k numbers of certification codes for verifying based on the OTP generating function for verifying which is stored in the memory of the user terminal, generates the k dimensional vector for verifying of which elements are the inverse numbers of the k numbers of certification codes for verifying, generates the k dimensional feedback vector by calculating Hadamard product between the k dimensional operation vector and the k dimensional vector for verifying, and then transmitting the k dimensional first feedback vector to the child care information platform server.

8. The operating method of claim 5, further comprising:

selecting, when the request to recommend an alternative child care product for a first category among the plurality of categories is received from the user terminal after the information of the recommended child care product for each of the categories is sent to the user terminal, an alternative child care product for the first category wherein the vector similarity between the 3 dimensional characteristic vector and the standard vector corresponded to the alternative child care product is the second biggest among the plurality of child care products included in the first category, and transmitting the information of the alternative child care product for the first category to the user terminal.

9. A non-transitory computer readable recording medium having a program recorded therein for allowing a computer to execute an operating method of a child care information platform server for recommending information regarding child care based on user information, the operating method comprising:

maintaining a child products information database in which information of a plurality of child products pre-classified by a predetermined plurality of categories based on the kinds of the plurality of child products and different predetermined standard vectors of each of the plurality of child products are stored, wherein the standard vectors are predetermined standard values to be used for selecting a recommended child product per each category;

receiving, when a request to recommend a child care product is received from a user terminal, n numbers of first information related to n numbers of predetermined questions about a mother's personal information, n numbers of second information related to n numbers of predetermined questions about a mother's health information, and n numbers of third information related to n numbers of predetermined questions about a child's health information, from a user terminal, wherein n is a natural number which is 2 or more;

converting the n numbers of first information to n numbers of first values based on a predetermined first conversion table, converting the n numbers of second information to n numbers of second values based on a predetermined second conversion table, and converting the n numbers of third information to n numbers of third values based on a predetermined third conversion table;

generating a matrix the size of 3×n, by allocating the n numbers of first values to the elements of the first line, allocating the n numbers of second values to the elements of the second line, and allocating the n numbers of third values to the elements of the third line;

generating a weighted value operation matrix the size of 3×1 by multiplying the matrix the size of 3×n by a predetermined a weighted value matrix the size of n×1, and then generating a 3 dimensional characteristic vector, of which the elements are the values included in the weighted value operation matrix the size of 3×1;

calculating, for each of the plurality of categories in the child products information database, the vector similarity between the 3 dimensional characteristic vector and each of the standard vectors of the plurality of baby products included in a category; and selecting a recommended child care product for each of the categories wherein the vector similarity between the 3 dimensional characteristic vector and the standard vector of the recommended child care product is the biggest among the plurality of child care products, and transmitting the information of the recommended child care product for each of the categories to the user terminal, wherein the vector similarity is calculated based on the Equation 1 below:

$$M = C + \frac{1}{D+1}, \quad \text{[Equation 1]}$$

wherein M means the vector similarity between two vectors, C means cosine similarity between the two vectors, and D means Euclidean distance between the two vectors.

* * * * *